United States Patent [19]

Atwall

[11] Patent Number: 4,654,335
[45] Date of Patent: Mar. 31, 1987

[54] ANTIHYPERTENSIVE 1,5-BENZOTHIAZEPINE DERIVATIVES, COMPOSITIONS, AND METHOD OF USE THEREFOR

[75] Inventor: Karnail Atwall, Cranbury, N.J.

[73] Assignee: E. R. Squibb & Sons, Inc., Princeton, N.J.

[21] Appl. No.: 753,760

[22] Filed: Jul. 11, 1985

[51] Int. Cl.$^4$ .................. A61K 31/38; A61K 31/55; C07D 281/10; C07D 281/08
[52] U.S. Cl. ................................. 514/211; 540/552
[58] Field of Search .............. 260/239 B, 330, 330.8; 544/62, 148, 376; 546/198; 548/518; 514/211; 540/552

[56] References Cited

U.S. PATENT DOCUMENTS 4,328,238  5/1982  Sato et al. ...................... 260/330

OTHER PUBLICATIONS

Medicinal Chemistry, Alfred Burger, 2nd Ed., Interscience Publishers, Inc., N.Y., 1960, pp. 566, 568, 580, 600 and 601.
Merck Index, 10th Edition, p. ONR-50, 51 (1983).

*Primary Examiner*—John M. Ford
*Assistant Examiner*—J. G. Mullins
*Attorney, Agent, or Firm*—Lawrence S. Levinson; Stephen B. Davis

[57] ABSTRACT

Compounds of formula

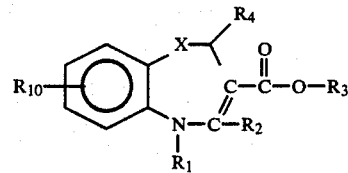

wherein X is S or $SO_2$, $R_4$ is aryl or hetero, and $R_1$ is hydrogen or

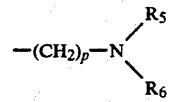

are disclosed. These compounds are useful as cardiovascular agents and especially as anti-hypertensive agents.

16 Claims, No Drawings

ANTIHYPERTENSIVE 1,5-BENZOTHIAZEPINE DERIVATIVES, COMPOSITIONS, AND METHOD OF USE THEREFOR

SUMMARY OF THE INVENTION

This invention relates to the novel 1,5-benzothiazepine compounds of formula I and pharmaceutically acceptable salts thereof

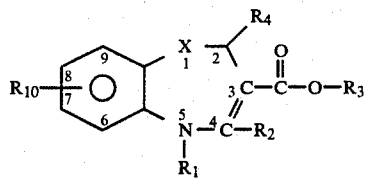

X is S or $SO_2$.
$R_1$ is hydrogen or

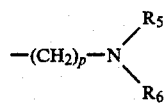

$R_2$ is hydrogen, lower alkyl, lower alkenyl, lower alkynyl, $-(CH_2)_m$-cycloalkyl, $-(CH_2)_m$-aryl, $-(CH_2)_m$-heterocyclo, $-(CH_2)_n-OH$, $-(CH_2)_n-O$-lower alkyl, $-(CH_2)_n-O-(CH_2)_m$-aryl, $-(CH_2)_n-SH$, $-(CH_2)_n-S$-lower alkyl, $-(CH_2)_n-S-(CH_2)_m$-aryl,

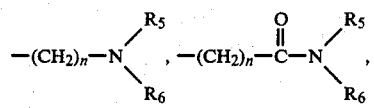

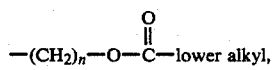

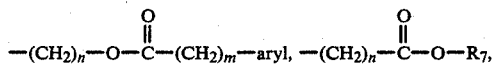

or halo substituted lower alkyl.

$R_3$ is hydrogen, lower alkyl, $-(CH_2)_m$-aryl, $-(CH_2)_m$-cycloalkyl, $-(CH_2)_n$-heterocyclo, $-(CH_2)_p-OH$, $-(CH_2)_p-O$-lower alkyl, $-(CH_2)_p-O-(CH_2)_m$-aryl, $-(CH_2)_p-SH$, $-(CH_2)_p-S$-lower alkyl, $-(CH_2)_p-S-(CH_2)_m$-aryl,

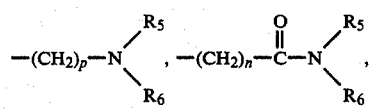

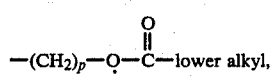

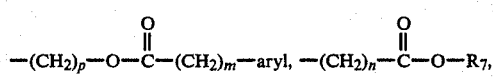

halo substituted lower alkyl, or a pharmaceutically acceptable salt forming ion.

$R_4$ is aryl or heterocyclo.

$R_5$ and $R_6$ are independently selected from the group consisting of hydrogen, lower alkyl, $-(CH_2)_m$-aryl,

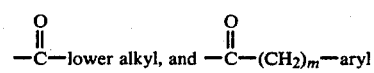

or $R_5$ and $R_6$ taken together with the N atom to which they are attached complete a heterocyclic ring of the formula

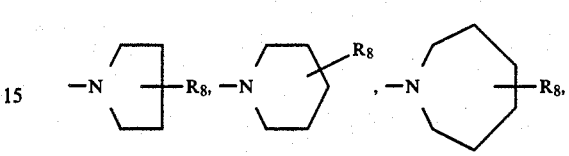

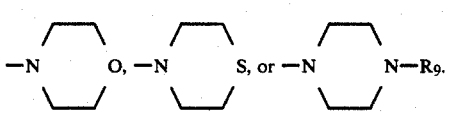

$R_7$ is hydrogen, lower alkyl, $-(CH_2)_m$-aryl, or a pharmaceutically acceptable salt forming ion.

$R_8$ is hydrogen, lower alkyl of 1 to 4 carbons, lower alkoxy of 1 to 4 carbons, lower alkylthio of 1 to 4 carbons, halo, $CF_3$ or hydroxy.

$R_9$ is hydrogen or lower alkyl of 1 to 4 carbons.

m is zero or an integer from 1 to 6.

n is an integer from 1 to 6.

p is an integer from 2 to 6.

$R_{10}$ is hydrogen, lower alkyl of 1 to 4 carbons, lower alkoxy of 1 to 4 carbons, halo, or $CF_3$.

DETAILED DESCRIPTION OF THE INVENTION

This invention in its broadest aspects relates to the 1,5-benzothiazepine compounds of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 4 to 7 carbon atoms with cyclopentyl and cylohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)₂ wherein alkyl is of 1 to 4 carbons, CF₃, NCS, OCHF₂,

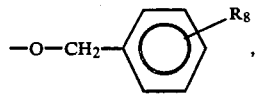

—O—CH₂-cycloalkyl,

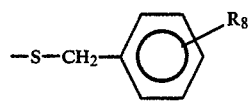

or —S—CH₂-cycloalkyl, di- or tri- substituted phenyl 1-naphthyl, or 2-naphthyl wherein said substituents are selected from methyl, methoxy, methylthio, halo, CF₃, nitro, hydroxy, amino, and OCHF₂, and pentafluorophenyl.

The term heterocyclo refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom in the benzene ring. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, NH-alkyl wherein alkyl is of 1 to 4 carbons, —N(alkyl)₂ wherein alkyl is of 1 to 4 carbons, CF₃, NCS, or OCHF₂ or such monocyclic and bicyclic rings wherein two or three available carbons have substituents selected from methyl, methoxy, methylthio, halo, CF₃, nitro, hydroxy, amino, and OCHF₂.

The compounds of formula I can be prepared as follows. For example, when X is sulfur and R₁ is hydrogen the 2-aminothiophenol of the formula

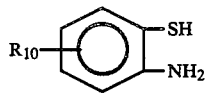

is treated with the keto ester compound of the formula

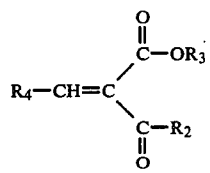

in a suitable solvent to give the desired compounds of formula I.

The compounds of formula I wherein R₁ is

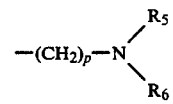

X is sulfur can be prepared by reacting the substituted aminothiophenol of the formula

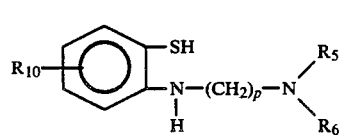

with the keto ester of formula III in a suitable solvent.

The compounds of formula I wherein X is SO₂ can be prepared by reacting the corresponding compound wherein X is sulfur with an oxidizing agent such as m-chloroperbenzoic acid.

The substituted aminothiophenol of formula IV can be prepared by reacting the unsubstituted starting material of formula II, i.e., R₁ is hydrogen, with carbodiimidazole to form the ketone of the formula

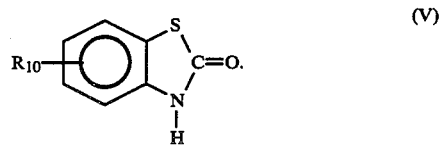

This ketone is then treated with the substituted amine

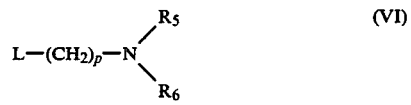

wherein L is a leaving group such as chloro, bromo, iodo, etc. to give the N-substituted ketone of the formula

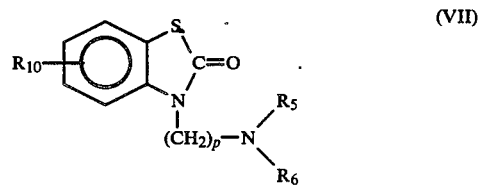

Treatment with potassium hydroxide and heat gives the desired starting material of formula IV.

If any of R₂, R₃, R₄, R₅ and R₆ in the above reactions are aryl or —(CH₂)ₘ-aryl wherein aryl is phenyl, 1- naphthyl or 2-naphthyl substituted with one or more hydroxy or amino groups, heterocyclo or —(CH$_2$)$_n$-heterocyclo wherein the heterocyclo ring contains an NH such as imidazolyl, or a substituted alkyl such as —(CH$_2$)$_n$—OH, —(CH$_2$)$_p$—OH, —(CH$_2$)$_p$—NH$_2$, —(CH$_2$)$_n$—SH, —(CH$_2$)$_p$—SH, or

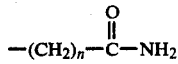

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:

R$_2$ is straight or branched chain lower alkyl of 1 to 5 carbons, especially methyl.

R$_3$ is straight or branched chain lower alkyl of 1 to 5 carbons, —(CH$_2$)$_p$—O-lower alkyl wherein lower alkyl is straight or branched chain of 1 to 5 carbons,

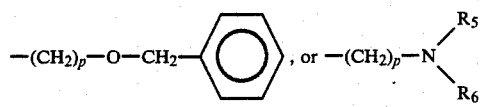

p is 2, 3 or 4.

R$_5$ and R$_6$ are independently selected from hydrogen, straight or branched chain lower alkyl of 1 to 5 carbons, and benzyl.

R$_4$ is phenyl, 2-, 3- or 4- mono substituted phenyl wherein said substituent is lower alkyl of 1 to 4 carbons, lower alkoxy of 1 to 4 carbons, lower alkylthio of 1 to 4 carbons, halo, CF$_3$, nitro, or OCHF$_2$, 2,3-disubstituted phenyl, 2,3,4-trisubstituted phenyl or 3,4,5-trisubstituted phenyl wherein said phenyl substitutents are selected from methyl, methoxy, methylthio, halo, CF$_3$, nitro and OCHF$_2$, or pentafluorophenyl.

R$_{10}$ is hydrogen or is at the 8-position and is methyl, methoxy, Cl, or CF$_3$.

Most preferred are the above compounds wherein:

R$_1$ is hydrogen or —(CH$_2$)$_2$—N(CH$_3$)$_2$.

R$_2$ is methyl.

R$_3$ is methyl or ethyl, especially methyl.

R$_4$ is phenyl, 2-nitrophenyl, 3-nitrophenyl, 4-nitrophenyl, 2-(trifluoromethyl)phenyl, 4-methylphenyl, 4-methoxyphenyl or 2,3-dichlorophenyl.

R$_{10}$ is hydrogen.

Especially these compounds wherein X is sulfur.

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which R$_2$ or R$_3$ is

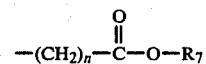

or in which R$_3$ is hydrogen include carboxylic acid salts, i.e., R$_3$ or R$_7$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg. per kilogram of body weight per day, preferably from about 1 to about 50 mg. per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

2,5-Dihydro-4-methyl-2-[2-(trifluoromethyl)phenyl]-1,5-benzothiazepine-3-carboxylic acid, methyl ester A solution of 2-[[2-(trifluoromethyl)phenyl]methylene]-3-oxobutanoic acid, methyl ester (1.8 g., 6.61 mmole) in dimethylformamide (5 ml.) is treated with 2-aminothiophenol (919 mg., 6.61 mmole) at room temperature. The reaction is stirred at room temperature for about 72 hours. The reaction is then heated at 65°-70° (oil bath temperature) for 10 hours. It is cooled to room temperature and diluted with ethyl acetate (50 ml.). The solution is thoroughly washed with water, sodium bicarbonate, and brine. After drying over anhydrous magnesium sulfate, the solvent is stripped off to give a yellow solid. Recrystallization from isopropyl ether-dichloromethane gives 783 mg. of product as fluffy needles. The mother liquor is purified by flash chromatography (20% ethyl acetate in hexane) and the resulting solid is recrystallized from isopropyl ether-dichloromethane to give 153 g. of additional product. Recrystallization from isopropyl ether-dichloromethane gives an analytically pure sample of 2,5-dihydro-4-methyl-2-[2-(trifluoromethyl)phenyl]-1,5-benzothiazepine-3-carboxylic acid, methyl ester; m.p. 165°–166.5°. TLC (silica gel, hexane: ethyl acetate, 60:40) $R_f=0.36$.

Anal. calc'd. for $C_{19}H_{16}F_3NO_2S$: C, 60.15; H, 4.25; N, 3.69; S, 8.45; F, 15.02. Found: C, 60.19; H, 4.22; N, 3.54; S, 8.41; F, 14.88.

EXAMPLE 2

2,5-Dihydro-4-methyl-2-phenyl-1,5-benzothiazepine-3-carboxylic acid, methyl ester A solution of 2-[(phenyl)methylene]-3-oxobutanoic acid, methyl ester (13.0 g., 63.7 mmole) in dry dimethylformamide (20 ml.) is treated dropwise with 2-aminothiophenol (8.85 g. of 90%, 63.7 mmole). A slight release of heat is noted. The reaction is stirred at room temperature for 6 hours and then heated at 65° for 72 hours. It is cooled to room temperature and diluted with ether. The resulting solution is thoroughly washed with water, sodium bicarbonate and brine. After drying over anydrous magnesium sulfate, the solvent is stripped off to give a yellow solid. It is triturated with isopropyl ether and filtered off to provide 6.93 g. of light yellow crystals. Recrystallization from isopropyl ether-dichloromethane gives an analytically pure sample of 2,5-dihydro-4-methyl-2-phenyl-1,5-benzothiazepine-3-carboxylic acid, methyl ester; m.p. 154°–156°. TLC(silica gel, hexane:acetone, 70:30) $R_f=0.35$.

Anal calc'd. $C_{18}H_{17}NO_2S$: C, 69,43; H, 5.50; N, 4.50; S, 10.30. Found: C, 69.52; H, 5.47; N, 4.35; S, 10.11.

EXAMPLE 3

2,5-Dihydro-4-methyl-2-(3-nitrophenyl)-1,5-benzothiazepine-3-carboxylic acid, methyl ester A suspension of 2-[(3-nitrophenyl)methylene]-3-oxobutanoic acid, methyl ester (2.0 g., 8.03 mmole) in dry dimethylformamide (7 ml.) is treated with 2-aminothiophenol (1.104 g. of 90%, 8.83 mmole). The resulting yellow solution is stirred at room temperature for one hour whereby the reaction becomes heterogeneous. It is heated at 65°–70° for 48 hours and then cooled to room temperature. The reaction is diluted with ether and washed with water, sodium bicarbonate, and brine, and is dried over anhydrous magnesium sulfate. Evaporation provides a yellow foam that is triturated with ether-hexane to give 1.85 g. of yellow crystalline product. Recrystallization from dichloromethane-isopropyl ether gives 1.3 g. of 2,5-dihydro-4-methyl-2-(3-nitrophenyl)-1,5-benzothiazepine-3-carboxylic acid, methyl ester as yellow needles; m.p. 139.5°–141.5°. TLC (silica gel, ethyl acetate: hexane, 40:60) $R_f=0.35$.

Anal. calc'd. for $C_{18}H_{16}N_2O_4S$: C, 60.66; H, 4.53; N, 7.86; S, 9.00. Found: C, 60.46; H, 4.50; N, 7.72; S, 8.94.

EXAMPLE 4

2,5-Dihydro-4-methyl-2-(4-methylphenyl)-1,5-benzothiazepine-3-carboxylic acid, methyl ester A solution of 2-[(4-methylphenyl)methylene]-3-oxobutanoic acid, methyl ester (1.09 g., 5 mmole) in dry dimethylformamide (5 ml.) is treated with 2-aminothiophenol (695 mg., 5 mmole). The resulting solution is stirred at room temperature for one hour. Acetic acid (0.3 ml., about 5 mmole) is then added and the reaction mixture is heated at 60°–65° for 24 hours. The reaction is allowed to cool down to room temperature, diluted with ether, and washed thoroughly with water, 1N sodium hydroxide, and brine. After drying over anhydrous magnesium sulfate, the solvent is stripped off to give a yellow foamy residue. Trituration with isopropyl ether gives 610 mg. of a colorless crystalline product. This material is twice recrystallized from ether-dichloromethane to give an analytically pure sample of 2,5-dihydro-4-methyl-2-(4-methylphenyl)-1,5-benzothiazepine-3-carboxylic acid, methyl ester; m.p. 148°–149.5°. TLC (silica gel; acetone:hexane, 30:70) $R_f=0.37$.

Anal. calc'd. for $C_{19}H_{19}NO_2S$: C, 70.13; H, 5.89; N, 4.30; S, 9.85. Found: C, 70.06; H, 5.90; N, 4.06; S, 9.89.

EXAMPLE 5

2,5-Dihydro-4-methyl-2-(4-nitrophenyl)-1,5-benzothiazepine-3-carboxylic acid, methyl ester A solution of 2-[(4-nitrophenyl)methylene]-3-oxobutanoic acid, methyl ester (1.295 g., 5 mmoles) in dimethylformamide (5 ml.) is treated with 2-aminothiophenol (695 mg. of 90%, 5 mmoles). After stirring the reaction at room temperature for one hour, it is heated at 60°–65° for 24 hours. The reaction is allowed to cool down to ambient temperature and diluted with ether. The resulting yellow solution is washed thoroughly with water, 1N sodium hydroxide, and brine. After drying over anhydrous magnesium sulfate, the solvent is stripped off to give a yellow foam (1.3 g.). This product is purified by flash chromatography (20% ethyl acetate in hexane) and the residue is recrystallized from isopropyl ether-dichloromethane to provide 2,5-dihydro-4-methyl-2-(4-nitrophenyl)-1,5-benzothiazepine-3-carboxylic acid, methyl ester as yellow needles; m.p. 149.5°–151.5° (sinters at 140°). TLC (silica gel; acetone:hexane, 30:70) $R_f=0.30$.

Anal. calc'd. for $C_{18}H_{16}N_2O_4S$: C, 60.66; H, 4.53; N, 7.86; S, 9.00. Found: C, 60.50; H, 4.50; N, 7.77; S, 8.95.

EXAMPLE 6

2,5-Dihydro-2-(4-methoxyphenyl)-4-methyl-1,5-benzothiazepine-3-carboxylic acid, methyl ester A solution of 2-[(4-methoxyphenyl)methylene]-3-oxobutanoic acid, methyl ester (1.17 g., 5 mmole) in dimethylformamide (5 ml.) is treated with 2-aminothiophenol (695 mg., 5 mmole) and the resulting yellow solution is allowed to stir at room temperature for one hour. It is then treated with acetic acid (0.3 ml., about 5 mmoles) and the reaction is allowed to warm up to 65°. Stirring is continued at this temperature for 24 hours. After cooling to room temperature, the reaction is diluted with ether and washed with water (5×20 ml.), sodium bicarbonate, and brine, and is then dried over anhydrous magnesium sulfate. Evaporation provides a yellow foam which is dissolved in isopropyl ether and allowed to sit under refrigeration for several days. A light yellow crystalline product forms (410 mg.). Recrystallization from isopropyl ether gives an analytically pure sample of 2,5-dihydro-2-(4-methoxyphenyl)-4-methyl-1,5-benzothiazepine-3-carboxylic acid, methyl ester; m.p. 107°–109.5°. TLC (silica gel; ethyl acetate:-hexane, 50:50) $R_f=0.50$.

Anal. calc'd. for $C_{19}H_{19}NO_3S$: C, 66.84; H, 5.61; N, 4.10; S, 9.39. Found: C, 66.71; H, 5.84; N, 3.97; S, 9.33.

EXAMPLE 7

2,5-Dihydro-4-methyl-2-(2-nitrophenyl)-1,5-benzothiazepine-3-carboxylic acid, methyl ester A solution of 2-[(2-nitrophenyl)methylene]-3-oxbutanoic acid, methyl ester (2.9 g., 11.6 mmole) in dimethylformamide (10.0 ml.) is treated with 2-aminothiophenol (1.45 g., 11.6 mmole). The reaction is stirred at room temperature for 4 hours. Acetic acid (0.2 ml.) is added and the reaction is heated at 65°–70° (oil bath temperature) for 24 hours. The reaction is cooled to ambient temperature and diluted with ether (70 ml.). The resulting solution is washed with sodium bicarbonate, water (5×15 ml.), and brine. After drying over anhydrous magnesium sulfate, the solvent is stripped off to give a yellow solid. This material is triturated with isopropyl ether to provide 2.63 g. of yellow crystalline product homogeneous by TLC. For analytical purposes, this material is recrystallized from dichloromethane-isopropanol to yield 2.1 g. of 2,5-dihydro-4-methyl-2-(2-nitrophenyl)-1,5-benzothiazepine-3-carboxylic acid, methyl ester as shiny yellow crystals; m.p. decomposition at 166°–172°. TLC (silica gel; ethyl acetate:hexane, 50:50) $R_f=0.45$.

Anal. calc'd. for $C_{18}H_{16}N_2O_4S$: C, 60.66; H, 4.53; N, 7.86; S, 9.00. Found: C, 60.88; H, 4.58; N. 7.85; S, 8.86.

EXAMPLE 8

2,5-Dihydro-4-methyl-2-(2,3-dichlorophenyl)-1,5-benzothiazepine-3-carboxylic acid, methyl ester A solution of 2-[(2,3-dichlorophenyl)methylene]-3-oxobutanoic acid, methyl ester (1.0 g., 3.66 mmole) in dry dimethylformamide (7 ml.) is treated with 2-aminothiophenol (512 mg., 4.1 mmoles) and the resulting reaction mixcture is stirred at room temperature for 3 hours. Acetic acid (0.1 ml.) is added and the reaction is heated at 75° (oil bath temperature) for 48 hours. It is then cooled to room temperature and diluted with ether. The resulting solution is washed with 1N sodium hydroxide, water, and brine. After drying over anhydrous magnesium sulfate, the solvent is stripped off to provide a yellow solid. It is crystallized from isopropyl ether-dichloromethane to yield 660 mg. of light yellow crystalline product. Recrystallization from isopropyl ether-dichloromethane yields an analytically pure sample of 2,5-dihydro-4-methyl-2-(2,3-dichlorophenyl)-1,5-benzothiazepine-3-carboxylic acid, methyl ester as colorless needles; m.p. 190°–191°. TLC (silica gel; ethyl acetate:hexanes, 40:60) $R_f=0.40$.

Anal. calc'd. for $C_{18}H_{15}Cl_2NO_2S$: C, 56.85; H, 3.98; N, 3.68; S, 8.43; Cl, 18.65. Found: C, 57.11; H, 4.09; N, 3,45; S, 8.39; Cl, 18.48.

EXAMPLE 9

5-[2-(Dimethylamino)ethyl]-2,5-dihydro-4-methyl-2-(3-nitrophenyl)-1,5-benzothiazepine-3-carboxylic acid, methyl ester, oxalate salt (1:1)

(a) Benzothiazolinone

A suspension of carbonyldiimidazole (15 g. 90%, 92.5 mmole) in anhydrous tetrahydrofuran (55 ml.) is cooled to 0° and treated dropwise with 2-aminothiophenol (11.6 g., 90%, 92.5 mmole). After the addition is completed, the yellow reaction mixture is stirred at room temperature overnight. It is then diluted with ethyl acetate (300 ml.) and washed with water, 2N hydrochloric acid (until acidic washings are obtained), sodium bicarbonate, and brine. After drying over anhydrous magnesium sulfate, the solvent is evaporated to give an off-white solid. It is triturated with isopropyl ether and filtered off (7.57 g.). The mother liquor is evaporated to give a yellow solid which is triturated with isopropyl ether and filtered to give a second crop of 2.04 g. The two crops are combined and recrystallized from dichloromethane-isopropyl ether to give an analytically pure sample of benzothiazolinone; m.p. 136°–138°. TLC (silica gel, ethyl acetate:hexane, 50:50) $R_f=0.53$.

Anal. calc'd. for $C_7H_5NOS$: C, 55.61; H, 3.33; N, 9.26; S, 21.21. Found: C, 55.39; H, 3.39; N, 9.02; S, 20.85.

(b) 3-(Dimethylaminoethyl)-2-benzothiazolinone

Freshly cut sodium metal (1.52 g., 66.23 g. atoms) is added in small pieces to absolute ethanol (100 ml.) at 0°. After stirring at 0° for one hour, the reaction is allowed to warm to room temperature whereby a clear solution is obtained. Benzothiazolinone (5.0 g., 33.1 mmole) is added in solid form. This is followed by the addition of N,N-dimethylaminoethyl hydrochloride (5.0 g., 34.7 mmoles). The resulting suspension is heated under reflux for 2 hours. It is allowed to cool down to room temperature and the white solid is filtered off and washed with more ethanol. Ethanol is stripped off and the residue is dissolved in ethyl acetate. It is then extracted with 1N hydrochloric acid (until acidic washings are obtained) and the combined extracts are basified (pH approximately 12) and reextracted with chloroform (3×70 ml.). The chloroform solution is washed with brine and dried over anhydrous magnesium sulfate. The solvent is then stripped off to give 5.68 g. of 3-(dimethylaminoethyl)-2-benzothiazolinone as a light pink oil. TLC (silica gel; dichloromethane:methanol:acetic acid, 18:1:1) $R_f=0.26$.

(c) 2-[(Dimethylaminoethyl)amino]-thiophenol

A solution of 3-(dimethylaminoethyl)-2-benzothiazolinone (5.0 g., 22.5 mmole) and potassium hydroxide (5.0 g., 89 mmole) in degassed ethanol (30 ml. of 90%) is heated under reflux for two hours. The yellowish reaction mixture is allowed to cool down to room temperature and the ethanol is stripped off. The residue is diluted with degassed water and neutralized with 15% acetic acid. The resulting solution is thoroughly extracted with chloroform (5×50 ml.) and the combined extracts are washed with brine, dried over anhydrous magnesium sulfate, and the solvent is stripped off to provide 3.8 g. of light yellow solid 2-[(dimethylaminoethyl)amino]thiophenol.

(d) 5-[2-(Dimethylamino)ethyl]-2,5-dihydro-4-methyl-2-(3-nitrophenyl)-1,5-benzothiazepine-3-carboxylic acid, methyl ester, oxalate salt (1:1)

A solution of 2-[(dimethylaminoethyl)amino]thiophenol (2.95 g., 12.6 mmole) in acetonitrile (15 ml.) is treated with methanolic hydrochloric acid (4 ml. of 3.5N solution). After about 30 minutes, the solvent is stripped off to provide a yellow foam. After subjecting it to a high vacuum for 30 minutes, it is dissolved in acetonitrile (15 ml.) and treated with 2-[(3-nitrophenyl)-methylene]-3-oxobutanoic acid, methyl ester (1.74 g., 6.98 mmole). The resulting suspension is stirred at room temperature for 12 hours resulting in a yellow solution. The solvent is removed under reduced pressure and the foamy residue (4.59 g.) is heated in dioxane:dimethylformamide (37 ml., 4:1) at 120° (oil bath temperature) for 24 hours. The red reaction mixture is cooled to ambient temperature and the dioxane is stripped off under vacuum. The residue is taken up in ethyl acetate and washed with 1N sodium hydroxide, water (5×20 ml.), and brine. After drying over anhydrous magnesium sulfate, the solvent is stripped off to give a dark oil. It is purified by flash chromatography (dichloromethane:methanol:acetic acid, 18:1:1) to provide 810 mg. of a yellow oil. The desired product is contaminated by two close running impurities. This material is dissolved in isopropanol and treated with oxalic acid (180 mg., 2 mmoles). A yellow precipitate is formed. It is filtered off and dissolved in hot ethanol. The resulting solution is allowed to cool gradually. The lower running impurity (TLC) precipitates out and is filtered off. The mother liquor is concentrated to give a yellow solid. The free amine is regenerated by partition between chloroform and 1N sodium hydroxide. This free amine is purified again by preparative TLC (dichloromethane:methanol:acetic acid, 20:1:1, run twice) to provide a yellow oil. This oil is taken up in isopropanol (5 ml.) and treated with oxalic acid. The yellow precipitate that forms is filtered off and recrystallized from isopropanol to give 5-[2-(dimethylamino)ethyl]-2,5-dihydro-4-methyl-2-(3-nitrophenyl)-1,5-benzothiazepine-3-carboxylic acid, methyl ester, oxalate salt (1:1); m.p. 141.5°–145°. TLC (silica gel; dichloromethane:methanol, 90:10) $R_f$=0.52.

Anal. calc'd. for $C_{22}H_{25}N_3O_4S \cdot C_2H_2O_4$: C, 55.70; H, 5.26; N, 8.12; S, 6.19. Found: C, 55.29; H, 5.19; N, 7.78; S, 6.10.

EXAMPLES 10–35

Following the procedure of Examples 1 to 9, the 2-aminothiophenol shown below in Col. I is reacted with the keto ester shown below in Col. II to give the product shown in Col. III.

| | Col. I | Col. II | Col. III | | |
|---|---|---|---|---|---|
| | (2-aminothiophenol structure with SH, N—$R_1$, H) | (keto ester structure with $R_4$—CH—C(=O)—$OR_3$ and C(=O)—$R_2$) | (benzothiazepine product with $R_{10}$, S, $R_4$, N—$R_{21}$, C(=O)—$OR_3$, C—$R_2$, positions 6,7,8,9) | | |
| Example | $R_1$ | $R_{10}$ | $R_2$ | $R_3$ | $R_4$ |
| 10 | —H | —Cl (8-position) | —$CH_3$ | —$CH_3$ | 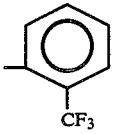 phenyl-$CF_3$ |
| 11 | —H | —$CH_3$ (8-position) | —$CH_3$ | —$C_2H_5$ | 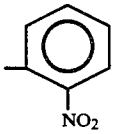 phenyl-$NO_2$ |
| 12 | —H | —$OCH_3$ (8-position) | —$CH_3$ | —$CH_3$ | 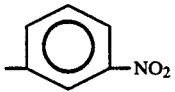 phenyl-$NO_2$ |
| 13 | —H | —$CF_3$ (8-position) | —$CH_3$ | —$CH_3$ | 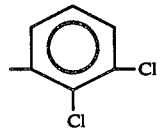 phenyl-Cl, Cl |
| 14 | —H | —H | —$CH_3$ | —$CH_3$ | 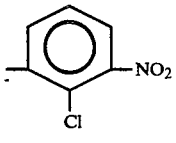 phenyl-$NO_2$, Cl |

-continued

| | Col. I | Col. II | Col. III | | |
|---|---|---|---|---|---|
| Example | R$_1$ | R$_{10}$ | R$_2$ | R$_3$ | R$_4$ |
| 15 | —H | —H | —CH$_3$ | —CH$_2$—O—CH$_2$—C$_6$H$_5$ | pentafluorophenyl |
| 16 | —H | —H | —CH$_3$ | —(CH$_2$)$_2$—N(CH$_3$)(CH$_2$C$_6$H$_5$) | 2-nitrophenyl |
| 17 | —H | —H | —CH$_3$ | —C$_2$H$_5$ | 6-nitronaphthyl |
| 18 | —H | —Cl (8-position) | —CH$_3$ | —CH$_2$—CH—(CH$_3$)$_2$ | 6-(trifluoromethyl)naphthyl |
| 19 | —H | —H | —CH$_3$ | —CH$_3$ | 2-(methylthio)pyridin-3-yl |
| 20 | —H | —H | —CH$_3$ | —(CH$_2$)$_2$—S—CH$_3$ | thien-2-yl |
| 21 | —H | —H | —CH$_3$ | —(CH$_2$)$_2$—S—C$_6$H$_5$ | 1-benzylimidazol-yl |
| 22 | —H | —H | —CH$_3$ | —(CH$_2$)$_2$—N(CH$_3$)$_2$ | 1-benzyl-4-methylindol-yl |

4,654,335
-continued
| | Col. I<br>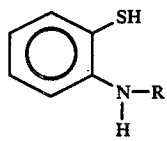 | | Col. II<br>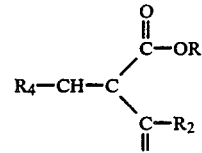 | Col. III<br>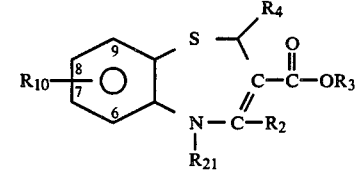 | |
|---|---|---|---|---|---|
| Example | $R_1$ | $R_{10}$ | $R_2$ | $R_3$ | $R_4$ |
| 23 | —H | —H | —CH$_3$ | —CH$_2$—C(O)—N(CH$_3$)$_2$ |  |
| 24 | —H | —H | —CH$_2$—C$_6$H$_5$ | —CH$_3$ | 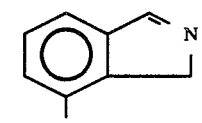 |
| 25 | —H | —H | —CF$_3$ | —C$_2$H$_5$ | 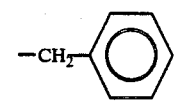 |
| 26 | —H | —H | —CH$_2$—O—CH$_3$ | —CH$_3$ | 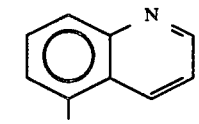 |
| 27 | —H | —H | —CH$_2$—O—C$_6$H$_5$ | —CH$_3$ | 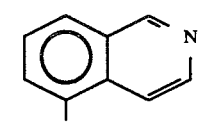 |
| 28 | —H | —H | —CH$_2$—S—C$_2$H$_5$ | —CH$_3$ | 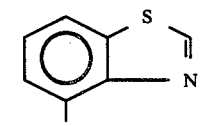 |
| 29 | —H | —H | —CH$_2$—S—CH$_2$—C$_6$H$_5$ | —CH$_3$ | 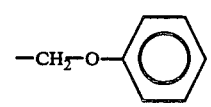 |
| 30 | —H | —H | —CH$_3$ | —CH$_3$ | 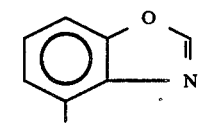 |
| 31 | —(CH$_2$)$_2$—N(CH$_3$)—CH$_2$—C$_6$H$_5$ | —H | —CH$_3$ | —CH$_3$ | 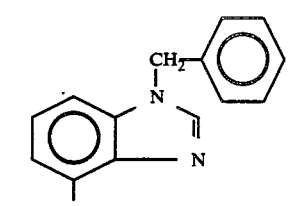 |

-continued

| | Col. I | Col. II | Col. III |
|---|---|---|---|

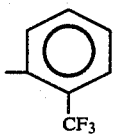

| Example | $R_1$ | $R_{10}$ | $R_2$ | $R_3$ | $R_4$ |
|---|---|---|---|---|---|
| 32 | —(CH$_2$)$_2$—N(C$_2$H$_5$)$_2$ | —H | —CH$_3$ | —CH$_3$ | 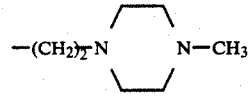 |
| 33 | 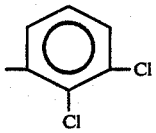 | —H | —CH$_3$ | —CH$_3$ | 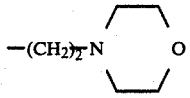 |
| 34 | 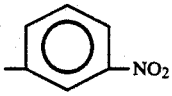 | —H | —CH$_3$ | —C$_2$H$_5$ | 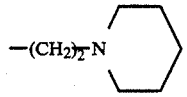 |
| 35 | 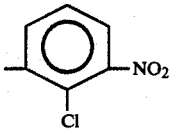 | —H | —CH$_3$ | —CH$_3$ | |

The N-protecting group in Examples 21, 22 and 28 are removed as the last step in the synthesis.

EXAMPLE 36

2,5-Dihydro-4-methyl-2-phenyl-1,5-benzothiazepine-3-carboxylic acid, methyl ester, 1,1-dioxide

A solution of 2,5-dihydro-4-methyl-2-phenyl-1,5-benzothiazepine-3-carboxylic acid, methyl ester (1.0 g., 3.21 mmole), prepared as set forth in Example 2, in dry dichloromethane (20 ml.) is treated with solid sodium bicarbonate (588 mg., 7.0 mmole). m-Chloroperbenzoic acid (1.41 g. of 85%, 7.0 mmoles) is added to the above suspension in small portions at 0°. After the addition is over, the reaction is allowed to warm to room temperature and stirred for 5 more hours. It is then diluted with ethyl acetate (100 ml.) and washed with 10% sodium bisulfate, 1N sodium hydroxide, and brine. After drying over anhydrous magnesium sulfate, the solvent is stripped off to provide 570 mg. of an off-white solid. This material is purified by flash chromatography (7% ethyl acetate in dichloromethane) and the colorless solid obtained is recrystallized from dichloromethane:ether to yield 332 mg. of 2,5-dihydro-4-methyl-2-phenyl-1,5-benzothiazepine-3-carboxylic acid, methyl ester, 1,1-dioxide; m.p. 223°–225° (decomposition). TLC (silica gel; ethyl acetate:hexane, 50:50) $R_f$=0.29.

Anal. calc'd. for C$_{18}$H$_{17}$NO$_4$S: C, 62.96; H, 4.99; N, 4.08; S, 9.34. Found: C, 63.09; H, 5.02; N, 3.77; S, 9.30.

In a similar manner, the products of Examples 1 and 3 to 35 can be converted to the corresponding 1,1-dioxide.

EXAMPLE 37

1000 tablets each containing the following ingredients:

| | |
|---|---|
| 2,5-Dihydro-4-methyl-2-[2-(trifluoromethyl)phenyl]-1,5-benzothiazepine-3-carboxylic acid, methyl ester | 100 mg. |
| Cornstarch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the 2,5-dihydro-4-methyl-2-[2-(trifluoromethyl)-phenyl]-1,5-benzothiazepine-3-carboxylic acid, methyl ester and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 36 can be prepared.

A similar procedure can be employed to form tablets containing 50 mg. of active ingredient.

EXAMPLE 38

Two piece #1 gelatin capsules are filled with a mixture of the following ingredients:

| | |
|---|---|
| 2,5-Dihydro-4-methyl-2-(3-nitrophenyl)-1,5-benzothiazepine-3-carboxylic acid, methyl ester | 50 mg. |
| Magnesium stearate | 7 mg. |
| Lactose | 193 mg. |
| | 250 mg. |

In a similar manner capsules containing 50 mg. of the product of any of Examples 1, 2, and 4 to 36 can be prepared.

EXAMPLE 39

An injectable solution is prepared as follows:

| | |
|---|---|
| 2,5-Dihydro-4-methyl-2-(2-nitrophenyl)-1,5-benzothiazepine-3-carboxylic acid, methyl ester | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 6 and 8 to 36.

EXAMPLE 40

1000 tablets each containing the following ingredients:

| | |
|---|---|
| 5-[2-(Dimethylamino)ethyl]-2,5-dihydro-4-methyl-2-(3-nitrophenyl)-1,5-benzothiazepine-3-carboxylic acid, methyl ester, oxalate salt (1:1) | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 5-[2-(dimethylamino)ethyl]-2,5-dihydro-4-methyl-2-(3-nitrophenyl)-1,5-benzothiazepine-3-carboxylic acid, methyl ester, oxalate salt (1:1), Avicel, and a portion of the stearic acid. The slugs are ground and passed through a #2 screen, then mixed with the hydrochlorothiazide, lactose, cornstarch, and reaminder of the stearic acid. The mixture is compressed into 350 mg. capsule shaped tablets in a tablet press. The tablets are scored for dividing in half.

In similar manner, tablets can be prepared containing 100 mg. of the product of any of Examples 1 to 8 and 10 to 36.

What is claimed is:

1. A compound of the formula:

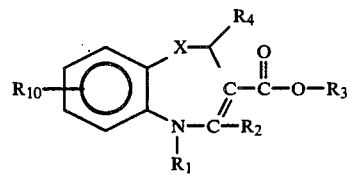

including a pharmaceutically acceptable salt thereof wherein:

X is S or $SO_2$;

$R_1$ is hydrogen or

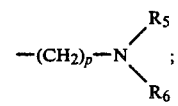

$R_2$ is straight or branched chain lower alkyl of 1 to 5 carbons;

$R_3$ is straight or branched chain lower alkyl of 1 to 5 carbons, $-(CH_2)_p-O$-lower alkyl wherein lower alkyl is straight or branched chain of 1 to 5 carbons,

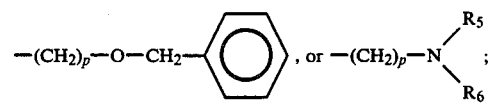

p is 2, 3 or 4;

$R_4$ is phenyl, 2-, 3- or 4-mono substituted phenyl wherein said substituent is lower alkyl of 1 to 4 carbons, lower alkoxy of 1 to 4 carbons, lower alkylthio of 1 to 4 carbons, halo, $CF_3$, nitro or $OCHF_2$, 2,3-disubstituted phenyl, 2,3,4-trisubstituted phenyl, or 3,4,5-trisubstituted phenyl wherein said phenyl substituents are selected from the group consisting of methyl, methoxy, methylthio, halo, $CF_3$, nitro and $OCHF_2$, or pentafluorophenyl;

$R_5$ and $R_6$ are independently selected from the group consisting of hydrogen, straight or branched chain lower alkyl of 1 to 5 carbons, and benzyl; and $R_{10}$ is hydrogen, methyl, methoxy, chloro, or $CF_3$.

2. A compound of claim 1 of the formula

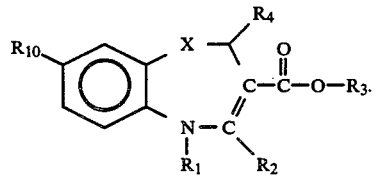

3. A compound of claim 2 wherein:

$R_1$ is hydrogen or $-(CH_2)_2-N(CH_3)_2$;

$R_2$ is methyl;

$R_3$ is methyl or ethyl;

$R_4$ is phenyl, 2-nitrophenyl, 3-nitrophenyl, 4-nitrophenyl, 2-(trifluoromethyl)phenyl, 4-methylphenyl, 4-methoxyphenyl, or 2,3-dichlorophenyl; and $R_{10}$ is hydrogen.

4. A compound of claim 3 wherein:
X is S.

5. The compound of claim 4 wherein:
$R_1$ is hydrogen;
$R_3$ is methyl; and
$R_4$ is 2-(trifluoromethyl)phenyl.

6. The compound of claim 4 wherein:
$R_1$ is hydrogen;
$R_3$ is methyl; and
$R_4$ is phenyl.

7. The compound of claim 4 wherein:
$R_1$ is hydrogen;
$R_3$ is methyl; and
$R_4$ is 3-nitrophenyl.

8. The compound of claim 4 wherein:
$R_1$ is hydrogen;
$R_3$ is methyl; and
$R_4$ is 4-methylphenyl.

9. The compound of claim 4 wherein
$R_1$ is hydrogen;
$R_3$ is methyl; and
$R_4$ is 4-nitrophenyl.

10. The compound of claim 4 wherein:
$R_1$ is hydrogen;
$R_3$ is methyl; and
$R_4$ is 4-methoxyphenyl.

11. The compound of claim 4 wherein:
$R_1$ is hydrogen;
$R_3$ is methyl; and
$R_4$ is 2-nitrophenyl.

12. The compound of claim 4 wherein:
$R_1$ is hydrogen;
$R_3$ is methyl; and
$R_4$ is 2,3-dichlorophenyl.

13. The compound of claim 4 wherein:
$R_1$ is $-(CH_2)_2-N(CH_3)_2$;
$R_3$ is methyl; and
$R_4$ is 3-nitrophenyl.

14. The compound of claim 3 wherein:
X is $SO_2$;
$R_1$ is hydrogen;
$R_3$ is methyl; and
$R_4$ is phenyl.

15. A composition useful in reducing blood pressure in a mammal comprising a pharmaceutically acceptable carrier and an anti-hypertensively effective amount of a compound or pharmaceutically acceptable salt thereof of the formula

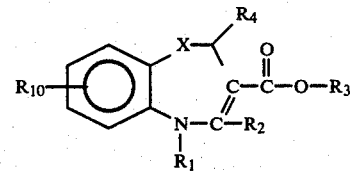

wherein X, $R_1$, $R_2$, $R_3$, $R_4$, and $R_{10}$ are as defined in claim 1.

16. The method of reducing blood pressure in a mammal comprising administering an effective amount of the composition of claim 15.

* * * * *